United States Patent [19]

Barngrover et al.

[11] Patent Number: 4,950,158

[45] Date of Patent: Aug. 21, 1990

[54] BUMPER FOR ORTHODONTIC BRACKETS

[75] Inventors: Conrad A. Barngrover, San Dimas; James D. Cleary, Glendora; Thomas M. Olsen, Alta Loma, all of Calif.

[73] Assignee: Unitek Corporation, Monrovia, Calif.

[21] Appl. No.: 267,570

[22] Filed: Nov. 7, 1988

[51] Int. Cl.$^5$ .............................................. A61D 3/00
[52] U.S. Cl. ........................................ 433/11; 433/18
[58] Field of Search ..................... 433/11, 13, 18, 15

[56] References Cited

U.S. PATENT DOCUMENTS 3,913,228  10/1975  Wallshein ........................ 32/14 A
4,054,997  10/1977  Wallsheim ........................... 433/11

OTHER PUBLICATIONS

Sales brochure "A" Company, San Diego, CA (copyright 1986).

Pp. 8-2 to 8-4 Orthodontic Catalog No. 122 of Unitek Corp., Monrovia, CA (copyright 1989).

Primary Examiner—Cary E. Stone
Attorney, Agent, or Firm—Donald M. Sell; Walter N. Kirn; James D. Christoff

[57] ABSTRACT

A preformed, elastomeric orthodontic ligature includes a molded protrusion or bumper portion integrally connected to an occlusal region of a ring portion of the ligature. When the ligature is connected to a bracket, the bumper portion extends over occlusal surfaces of the bracket including an occlusal tie wing in order to prevent direct contact of the bracket with an opposing tooth. In preferred embodiments, the bumper portion is connected to the ring portion by a thin web which is configured to enable the ring portion to firmly seat under the tie wing and also enables the bumper portion to conform to the occlusal surfaces of the bracket such that the ring portion does not normally stretch and disengage the tie wings during mastication.

10 Claims, 1 Drawing Sheet

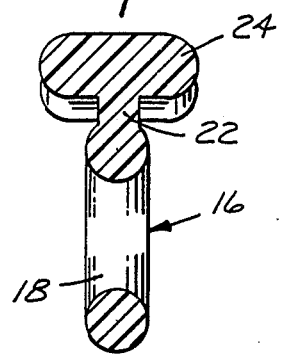
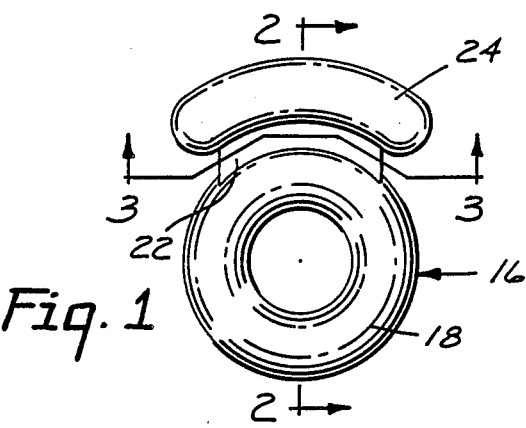
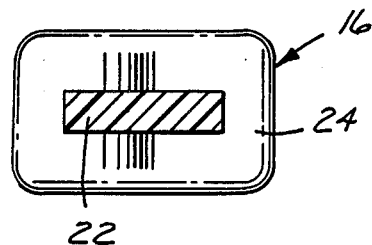
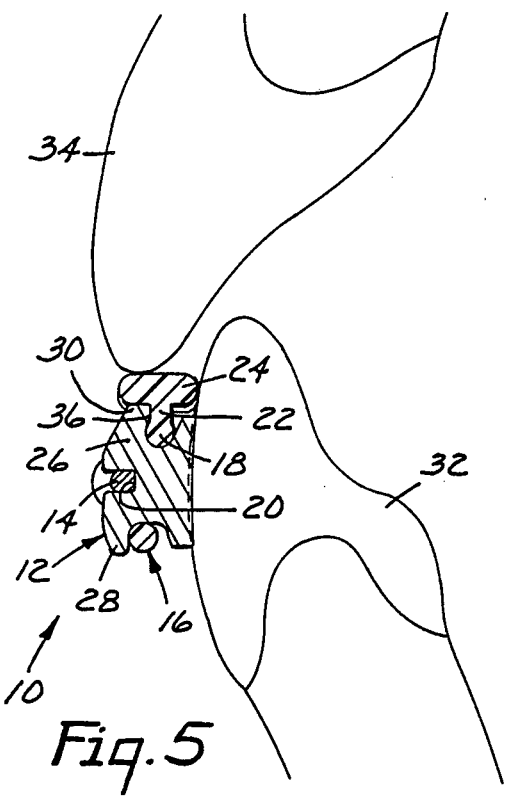
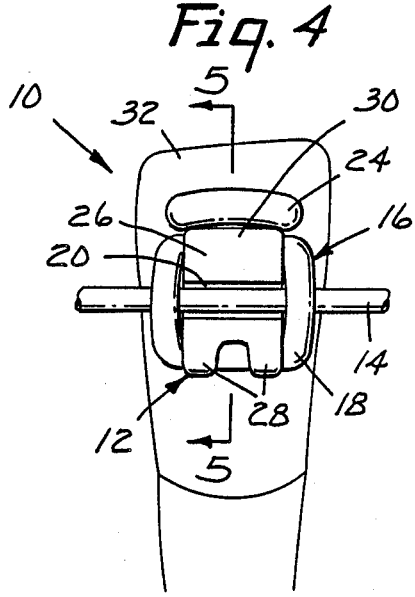

BUMPER FOR ORTHODONTIC BRACKETS

BACKGROUND OF THE INVENTION

1. Field of the Invention

This invention relates to an elastomeric orthodontic ligature having a protruding bumper portion to prevent the associated bracket from damaging opposing teeth

2. Description of the Related Art

Elastomeric ring-shaped ligatures are in widespread use for retaining archwire in the slots of orthodonic brackets. Each ligature when installed is stretched over occlusal and gingival tie wings of the bracket and toward a recess behind the tie wings, with side portions of the ligature extending around the archwire to retain the archwire securely seated in the bracket slot.

In orthodontic treatment, the lower tips of upper anterior teeth may, in certain instances, come into contact with the upper or occlusal surface of brackets mounted on corresponding, lower anterior teeth. In these instances, the brackets may cause wear and abrasive damage to the enamel of the occluding teeth This problem is particularly apparent when the brackets are formed from a ceramic material which is typically much harder than the material forming conventional metallic brackets.

SUMMARY OF THE INVENTION

The present invention is directed toward an orthodontic assembly which includes a bracket having an archwire slot, tie wing means and an occlusal section The assembly also includes an archwire and an elastomeric ligature connected to the tie wing means for retaining the archwire in a position at least partially in the slot. Advantageously, the elastomeric ligature includes an enlarged bumper portion disposed occlusally of the occlusal section of the bracket for substantially preventing contact of the bracket with opposing teeth.

In particularly preferred forms of the invention, the bumper portion is integrally connected by a web to a ring-shaped portion of the ligature. The web is somewhat thinner than either the bumper portion or the ring-shaped portion and is complemental in configuration to the occlusal tie wing, thereby enabling the ring portion to fully seat in a recess located behind the tie wing. In addition, the web permits the bumper portion to rock independently of the ring portion and enable the bumper portion to seat against and closely conform to the occlusal section of the bracket. By having the ring portion and bumper portion so seated, the ligature will not, in all likelihood, inadvertently roll off of the bracket during mastication.

BRIEF DESCRIPTION OF THE DRAWINGS

FIG. 1 is a front elevational view of an elastomeric ligature constructed in accordance with the principles of the present invention;

FIG. 2 is a side cross-sectional view of the ligature taken along lines 2—2 of FIG. 1;

FIG. 3 is a cross-sectional view of the ligature taken substantially along lines 3—3 of FIG. 1;

FIG. 4 is a reduced, front elevational view of an orthodontic assembly of the present invention which includes the elastomeric ligature of FIGS. 1—3 as well as an archwire and an orthodontic bracket which is affixed to a tooth; and FIG. 5 is a side cross-sectional view of the assembly illustrated in FIG. 4, showing for exemplary purposes a representative position of an opposing tooth which is prevented by an enlarged bumper portion of the ligature from contacting the bracket.

DESCRIPTION OF THE PREFERRED EMBODIMENT

An orthodontic assembly 10 in accordance with the invention is shown in FIGS. 4 and 5 and broadly includes a bracket 12, an archwire 14 and a ligature 16. The ligature 16 is also shown in FIGS. 1-3 and includes a normally O-shaped ring portion 18 for retaining the archwire 14 in a front, mesially-distally extending archwire slot 20 of the bracket 12.

The ring portion 18 of the ligature 16 has an occlusal side which is integrally connected with a web 22. In turn, the web 22 is integrally coupled with an enlarged bumper portion 24 that has an oval-shaped cross section (see FIGS. 2 and 5) which is somewhat wider than the ring portion 18 and the web 22.

The ligature 16 is made of elastomeric materials used to mold conventional O-ring ligatures. The ligature 16 in its relaxed or unstretched condition has a configuration as illustrated in FIGS. 1-3 wherein the ring portion 18 is in the shape of a circle and the bumper portion 24 extends generally in a mesial-distal direction disposed occlusally of the web 22 and ring portion 18, with the bumper portion 24 extending in an arc concentric with the curvature of the ring portion 18.

When the ligature 16 is connected to the bracket 12 as depicted in FIGS. 4 and 5, an occlusal region of the ring portion 18 is seated in a ligature recess behind an occlusal tie wing 26, while the gingival region of the ring portion 18 is seated in a ligature recess behind a pair of spaced apart gingival tie wings 28. Side regions of the ring portion 18 extend along mesial and distal sides respectively of the bracket 12 and also wrap partially around a labial side of the archwire 14 in order to retain the archwire 14 in the archwire slot 20.

The occlusal tie wing 26 of the bracket 12 presents an occlusalmost section 30 (FIG. 5) with an uppermost surface that is covered by the bumper portion 24. The elastic nature of the ligature 16 enables the normal curvature of the bumper portion 24 to flatten somewhat when installed on the bracket 12 such that the bumper portion 24 assumes the configuration shown in FIGS. 4 and 5 in substantial, if not complete contact with the top surface of the occlusal section 30, both in a mesial-distal direction as well as a buccal-lingual direction. Moreover, a buccal region of the bumper portion 24 overhangs the buccal edge of the occlusal section 30, while a lingual region of the bumper portion 24 contacts an adjacent section of a tooth 32 on which the bracket 12 is adhesively mounted. In this instance, tooth 32 represents a lower anterior tooth disposed beneath a corresponding, upper anterior tooth 34 (FIG. 5) when the jaw is closed.

As can be appreciated by reference to FIG. 5, the bumper portion 24 covers all occlusally-facing surfaces of the bracket 12 and thus prevents contact of the bracket 12 with the tip of the opposing tooth 34 when the jaw is closed. As a consequence, enamel damage to the tooth 34 as well as patient discomfort is largely avoided.

The web 22 of the ligature 16 is thinner in a buccal-lingual direction and in a mesial-distal direction than the bumper portion 24 as well as adjacent, interconnected regions of the ring portion 18. In addition, and as shown in FIG. 5, the web 22 is of a height sufficient to enable the adjacent, occlusal region of the ring portion 18 to firmly seat in the ligature recess behind the occlusal tie wing 26 while the bumper portion 24 is in contact with substantially the entire top surface of the occlusal section 30 of the bracket 12. Consequently, the web 22 functions to enable the bumper portion 24 to firmly seat against the occlusal section 30, and also permits the bumper portion 24 to rock or tilt independently of the ring portion 18 during mastication so that the ring portion 18 normally does not accidentally stretch, disengage the tie wings 26, 28 and roll off of the bracket 12 when the bumper portion 24 is subjected to occlusal forces by the opposing tooth 34.

In addition, the configuration of the web 22 is complemental to a lingual side 36 of the occlusal tie wing 26 facing the ligature recess as shown in FIG. 5. More specifically, the lingual side 36 extends in a direction toward the tooth 32 past the buccal side of the occlusal ligature recess, which further facilitates retention of the ring portion 18 in the ligature recess whenever the tooth 34 comes into contact with the bumper portion 24. As a result, there is little likelihood that the ligature 16 will become unintentionally disengaged from the bracket 12 in the period of time between appointments with the attending orthodontist.

We claim:

1. An orthodontic assembly comprising:
   a bracket having an archwire slot and tie wing means with an occlusal section;
   an archwire; and
   an elastomeric ligature connected to said tie wing means for retaining said archwire in a position at least partially in said slot, said ligature including an enlarged bumper portion disposed occlusally of said occlusal section for substantially preventing contact of said bracket with opposing teeth, said bumper portion extending in a buccal direction a distance sufficient to substantially cover said occlusal section.

2. The assembly of claim 1, wherein said ligature includes a ring portion and a web interconnecting said ring portion and said bumper portion.

3. The assembly of claim 2, wherein said web is thinner in a buccal-lingual direction than adjacent regions of said ring portion.

4. The assembly of claim 3, wherein said bumper portion is elongated and extends in a mesial-distal direction.

5. The assembly of claim 4, wherein said bumper portion is wider than said web in a mesial-distal direction.

6. The assembly of claim 1, wherein said bumper portion is of a configuration sufficient for substantially covering said occlusal section of said bracket.

7. The assembly of claim 1, wherein said bumper portion is in contact with substantially the entire extent of said occlusal section.

8. An elastomeric orthodontic ligature for use with an orthodontic bracket having occlusal tie wing means comprising:
   an archwire ligating ring portion having a certain, maximum buccal-lingual thickness;
   a web integrally coupled to said ring portion; and
   a bumper portion integrally connected to said web remote from said ring portion and having an overall buccal-lingual thickness greater than said certain thickness of said ring portion, said bumper portion extending in a buccal direction directly above said web for contact with an occlusal section of the tie wing means,
   said web being thinner in buccal-lingual direction than said certain thickness of said ring portion for facilitating movement of said bumper portion generally independent of said ring portion.

9. The ligature of claim 8, wherein said bumper portion normally extends in a direction generally concentric with said ring portion.

10. The ligature of claim 8, wherein said web presents a certain mesial-distal width, and wherein said bumper portion extends in a mesial-distal direction a distance greater than said width of said web.

* * * * *